United States Patent [19]
Braly

[11] Patent Number: 5,589,628
[45] Date of Patent: Dec. 31, 1996

[54] GOLF BALL STRIKING DEVICE

[75] Inventor: Joseph M. Braly, Kennett Square, Pa.

[73] Assignee: PGA Tour, Ponte Vedra, Fla.

[21] Appl. No.: 575,092

[22] Filed: Dec. 19, 1995

[51] Int. Cl.$^6$ .................................................. G01N 3/30
[52] U.S. Cl. ................................................. 73/12.02
[58] Field of Search ........................... 73/12.01, 12.02, 73/12.09, 12.14, 379.01, 379.02, 379.04; 473/257–260; 482/83, 84, 90, 909

[56] References Cited

U.S. PATENT DOCUMENTS

| | | | |
|---|---|---|---|
| 633,464 | 9/1899 | Melson | 73/379.04 X |
| 1,636,234 | 7/1927 | Klopsteg | 73/12.02 X |
| 1,975,368 | 10/1934 | Mikesell | 73/379.04 X |
| 1,987,859 | 1/1935 | Meyer | 73/379.04 |
| 1,995,170 | 3/1935 | Davis | 73/12.02 |
| 2,058,201 | 10/1936 | Young | 73/12.02 |
| 3,855,842 | 12/1974 | Imabori et al. | 73/12.02 X |
| 4,062,222 | 12/1977 | Solheim | 73/12.02 |
| 4,996,867 | 3/1991 | Miyamae | 73/12.02 X |

FOREIGN PATENT DOCUMENTS

0320049  9/1929  United Kingdom .................. 73/12.02

Primary Examiner—Richard Chilcot
Assistant Examiner—Elizabeth L. Dougherty
Attorney, Agent, or Firm—Connolly & Hutz

[57] ABSTRACT

A golf ball striking device has a framework with a club and shaft assembly rotatably mounted to the framework for movement along a swing path in a first vertical plane. A golf ball tee assembly is also rotatably mounted to the framework for free movement in a second vertical plane into any one of a plurality of positions, and structure is provided for releasability locking the golf ball tee assembly in place at the selected position. A golf ball tee is located at the outer end of the golf ball tee assembly for holding a golf ball in the first vertical plane in the swing path of the club and shaft assembly. A structural arrangement on the golf ball tee assembly maintains the tee vertical at any of the plurality of positions of the golf ball tee assembly. A motivator is connected to move the club and shaft assembly along its swing path for striking a golf ball on the tee.

17 Claims, 7 Drawing Sheets

GOLF BALL STRIKING DEVICE

BACKGROUND OF THE INVENTION

The present invention relates to a mechanical device for striking golf balls, and more particularly to a device that strikes golf balls under selected predetermined conditions for comparative testing and analytical purposes.

The overall design and construction of golf balls varies from one manufacture to the next, and the same is also true of the diverse methods utilized to produce golf balls. Tests show that some golf balls have a more accurate trajectory and/or travel a greater distance when compared to golf balls of different design and/or construction even when subjected to identical impact conditions. Variations in swing also produce trajectories that curve right or left and thereby cause hooks and slices.

Hence, there is a real need for a dependable golf ball striking device for use in testing and analyzing golf balls, and the present striking device is in response to that need.

SUMMARY OF THE INVENTION

Accordingly, it is an object of the present invention to provide a golf ball striking device which is relatively simple in design and easy to use and one which produces predetermined impact conditions.

Another object of the present invention is a golf ball striking device having a variety of adjustment mechanisms for changing the position of the golf ball along the swing path of the club head, changing the flight path of the golf ball, and changing the angle of impact of the club head on the golf ball to produce a slice or hook.

Another object of the present invention is a golf ball striking device which produces selected predetermined conditions for comparative testing of golf balls and analytical purposes.

In accordance with the present invention a golf ball striking device comprises a framework with a club and shaft assembly rotatably mounted to the framework for movement along a swing path in a first vertical plane. A golf ball tee assembly has upper and lower ends with the upper end rotatably mounted to the framework of the device for free movement of the golf ball tee assembly in a second vertical plane into any one of a plurality of positions. Structure is provided for releasably locking the golf ball tee assembly in place at any one of its plurality of positions. A golf ball tee is positioned at the lower end of the golf ball tee assembly for supporting a golf ball in the first vertical plane in the swing path of the club and shaft assembly. Structure on the golf ball tee assembly maintains the tee vertical at any of the plurality of positions of the golf ball tee assembly. Finally, a motivator is connected to move the club and shaft assembly along its swing path for striking a golf ball on the tee.

The club and shaft assembly has a horizontal axis of rotation and the golf ball tee assembly has the same axis of rotation. Preferably, the golf ball tee assembly includes adjusting structure for the golf ball tee for shifting the golf ball tee in a horizontal direction toward and away from the golf ball tee assembly.

The club and shaft assembly of the golf ball striking device includes a club head constructed and arranged to impact upon a golf ball on the tee of the golf ball tee assembly. The club head has an adjustable loft as well as structure for releasably locking the club head in place at any one of a plurality of selected club head lofts. Preferably, the club and shaft assembly includes a club shaft having a longitudinal axis about which that shaft rotates. The club head is fixedly connected to the club shaft at the lower end thereof. Rotation of the club shaft shifts the club head to the right or left to thereby produce a hook or slice upon impact with the golf ball on the tee. A pointer on the club shaft cooperates with a fixed angular scale for indicating the rotary position of the club shaft about its longitudinal axis.

Preferably, the golf ball striking device includes a tee angle position scale fixed to the framework for indicating the position of the golf ball on the swing path of the club and shaft assembly. The position scale has an arcuate slot, and tee guide retainers on the golf ball tee assembly extend into the arcuate slot for movement along the slot as the golf ball tee assembly is rotated to any one of its plurality of positions. Structure is provided on the tee guide retainers for releasably locking the golf ball tee assembly to the tee angle position scale. A pointer on the golf ball tee assembly cooperates with the fixed tee angle position scale for indicating the angular position of the golf ball tee assembly and the golf ball.

The framework of the golf ball striking device preferably includes a fixed lower base frame assembly and an upper frame with a vertical pivot pin interconnecting the upper frame with the fixed lower base frame assembly. The club and shaft assembly and the golf ball tee assembly are mounted to the upper frame for movement therewith about the vertical pivot pin. The upper frame has a pointer and the fixed lower base assembly has a scale for indicating the trajectory angle of the swing path of the club and shaft assembly. Structure is provided for releasably locking the upper frame to the fixed lower base frame assembly at the desired trajectory angle of the swing path of the club and shaft assembly.

The motivator of the golf ball striking device includes a servo motor and gear box with a shaft assembly interconnecting the servo motor and gear box to the shaft assembly. A flexible coupler is provided in the shaft assembly.

BRIEF DESCRIPTION OF THE DRAWINGS

Novel features and advantages of the present invention in addition to those mentioned above will become apparent to persons of ordinary skill in the art from a reading of the following detailed description in conjunction with the accompanying drawings wherein similar reference characters refer to similar parts and in which.

DETAILED DESCRIPTION OF THE INVENTION

Figure 1:
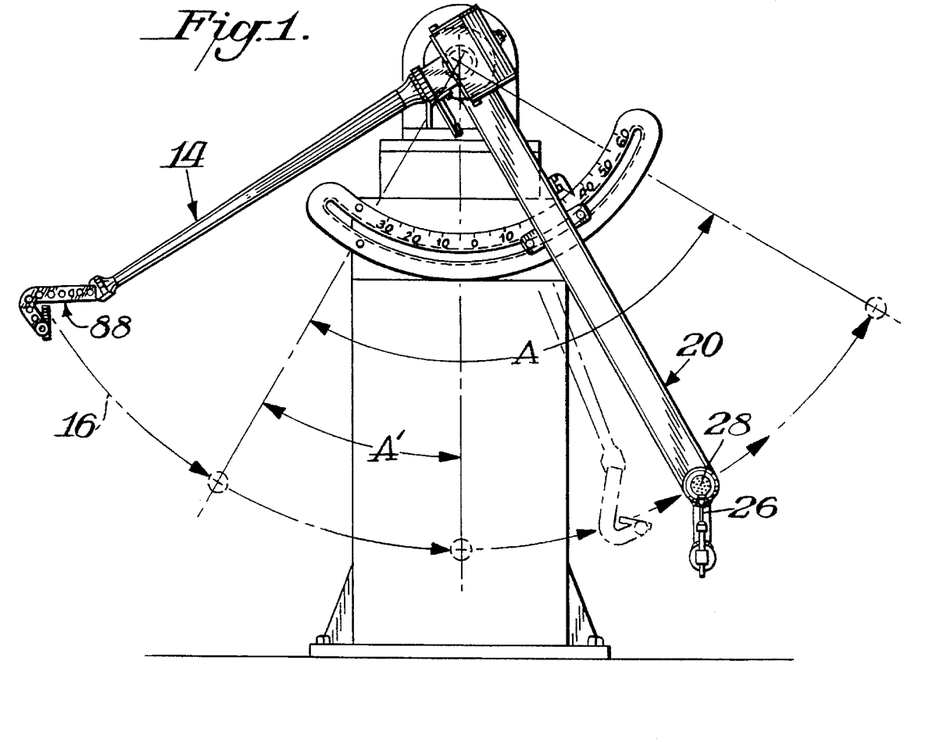
FIG. 1 is a front elevational view of a golf ball striking device, according to the present invention.
Figure 2:
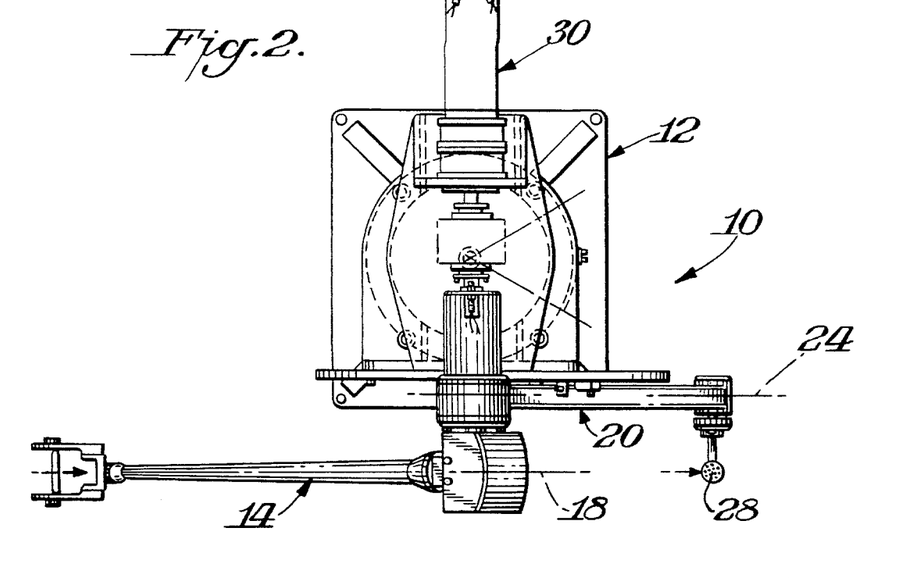
FIG. 2 is a top plan view of the golf ball striking device shown in FIG. 1.
Figure 3:
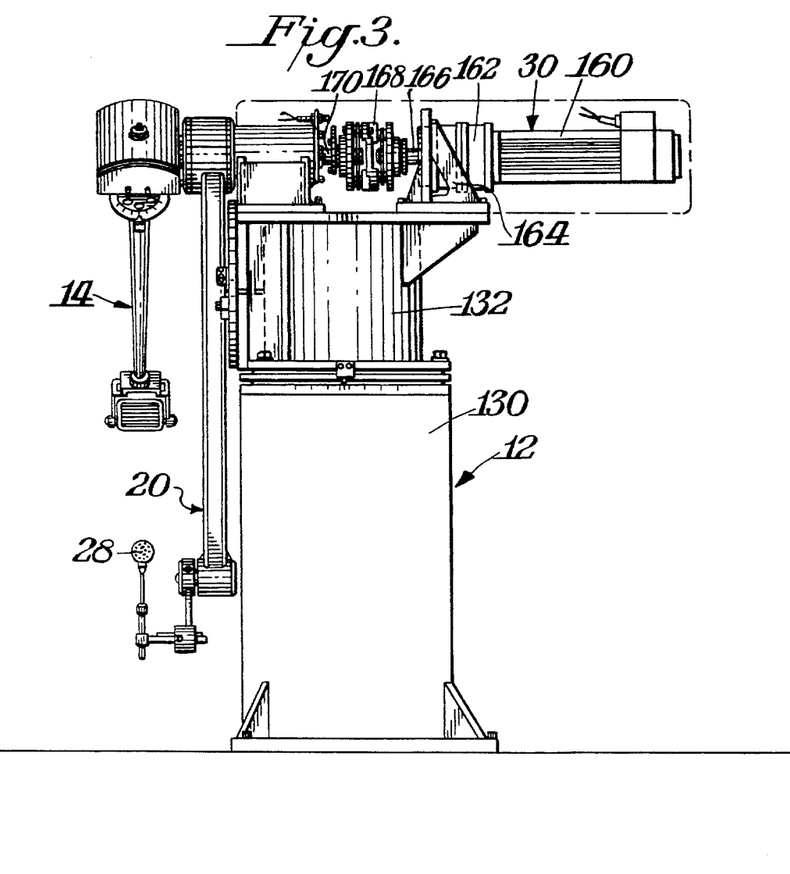
FIG. 3 is a right side elevational view of the golf ball striking device shown in FIGS. 1 and 2.
Figure 4:
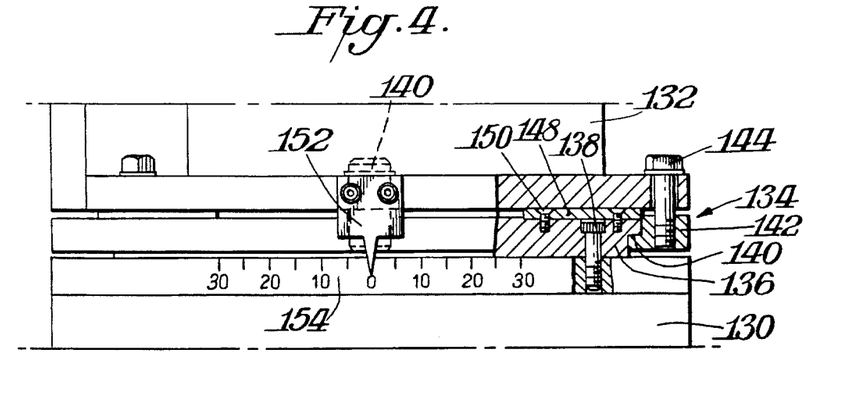
FIG. 4 is an enlarged fragmental side elevational view illustrating the trajectory angle scale of the golf ball striking device.

Referring in more particularity to the drawings, FIGS. 1–3 illustrate a golf ball striking device 10 comprising a framework 12 with a club and shaft assembly 14 rotatably mounted to the framework for driven movement along a swing path 16 in a first vertical plane 18. Golf ball striking device 10 further includes a golf ball tee assembly 20 having an upper end in the form of a bearing 22 rotatably mounted to framework 12 for free movement of the golf ball tee assembly in a second vertical plane 24 into any one of a plurality of positions. As explained more fully below, structure is provided for releasably locking golf ball tee assembly 20 in place at any one of its plurality of positions.

A golf ball tee 26 is positioned at the lower end of golf ball tee assembly 20 for supporting a golf ball 28 in first vertical plane 18 in swing path 16 of club and shaft assembly 14. Tee 26 may be somewhat flexible and fabricated of rubber or similar material. As explained more fully below, structure at the lower end of golf ball tee assembly 20 functions to maintain tee 26 vertical at any of the plurality of positions of the golf ball tee assembly. Finally, a motivator assembly 30 is connected to drive club and shaft assembly 14 along its swing path 16 for impacting golf ball 28 on tee 26.

The golf ball tee assembly of striking device 10 includes a main support arm 32 with the upper end of the arm terminating in bearing 22. The lower end of the support arm has an adjustment mechanism which functions to maintain golf tee 26 vertical at the various positions of golf ball tee assembly 20. This adjustment mechanism includes a lower support arm 34 rotatably connected to the main support arm by a bearing assembly 36 for free rotation about a horizontal axis 38. Golf ball tee 26 is secured to the lower support arm. Set screws 40 function to secure the lower support arm to a freely rotatable shaft 42 of the bearing assembly. In operation, gravity functions to maintain lower support arm 34 and the attached golf ball tee in a vertical position regardless of the location of golf ball tee assembly 20. As the golf ball tee assembly is rotated from one position to another, shaft 42 freely rotates in bearing assembly 26 to maintain tee 26 in a vertical position.

Figures 7, 8, 9:
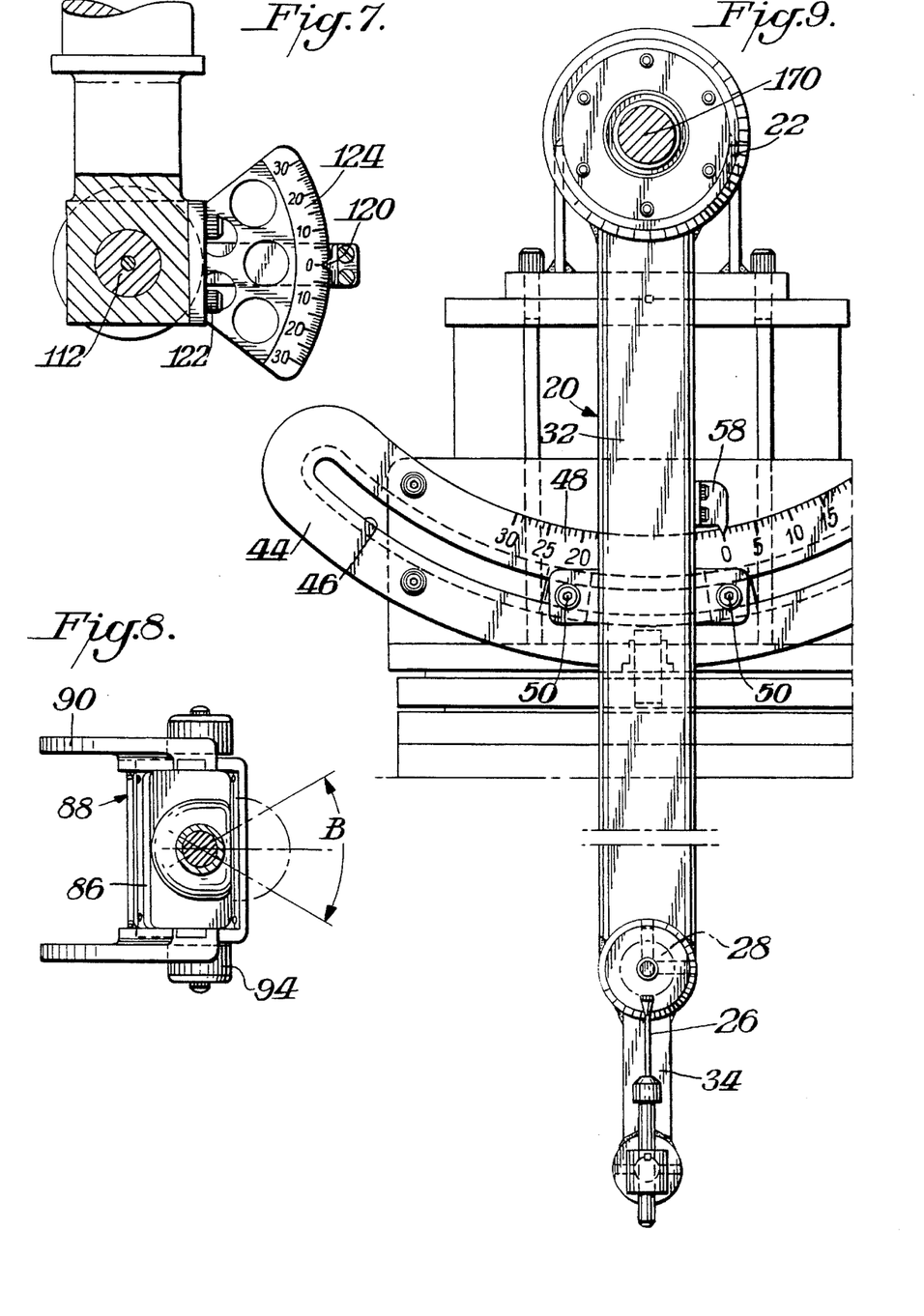
FIG. 7 is a cross-sectional plan view illustrating the hook and slice angle scale of the club and shaft assembly taken along line 7—7 of FIG. 5.
FIG. 8 is a cross-sectional plan view illustrating the club head of the club and shaft assembly taken along line 8—8 of FIG. 5.
FIG. 9 is a front elevational view of the golf ball tee assembly and angle scale of the golf ball striking device.
Figure 10:
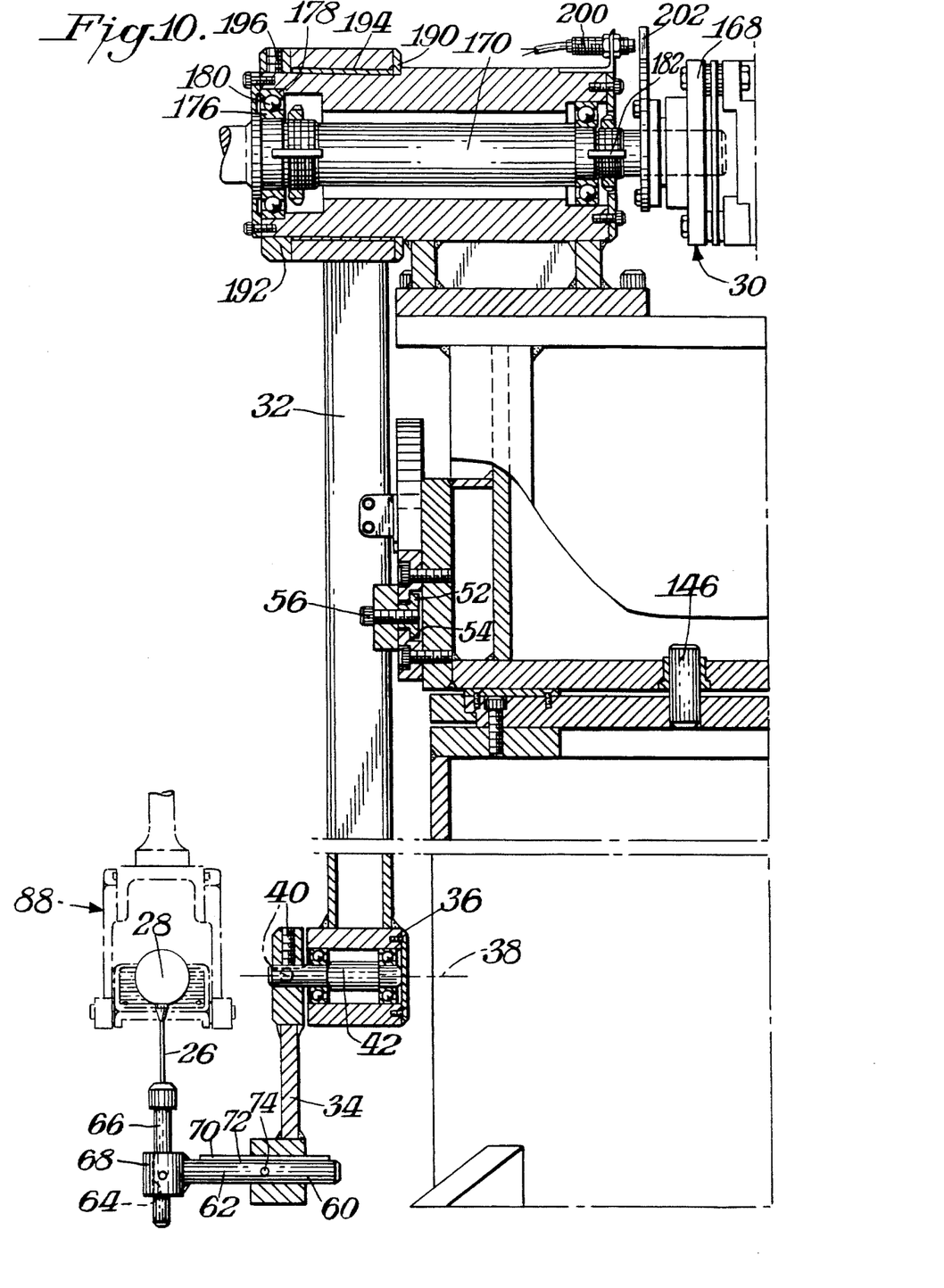
FIG. 10 is a right side elevational view partially broken away illustrating the golf ball tee assembly just prior to impact of the ball with the club head shown in phantom outline.

A support arm quadrant 44 is fixedly secured to the framework 12, as shown best in FIGS. 1, 9 and 10. The support arm quadrant has an arcuate slot 46 herein and a tee angle position scale 48 extends along the slot. Basically, the slot is designed to receive tee guide retainers 50 secured to the main support arm of golf ball tee assembly 18 for guiding that assembly and releasably locking it in place. The tee guide retainers extend into arcuate slot 46 for movement along the slot as golf ball tee assembly 20 is rotated to any one of its plurality of positions. Each tee guide retainer comprises a tee nut 52 fitted within a tee nut undercut 54 on the back side of the support arm quadrant. A bolt 56 extends through main support arm 32 and arcuate slot 46 into threaded engagement with the tee nut. Bolts 56 releasably lock golf ball tee assembly 20 to the support arm quadrant which is fixedly secured to framework 12.

A ball position pointer 58 is secured to main support arm 32 of golf ball tee assembly 20. Pointer 58 cooperates with tee angle position scale 48 on quadrant 44 for indicating the angular position of the golf ball tee assembly. Tee angle position scale 48 has indicia ranging from −30° to 60°, and the golf ball tee assembly is vertically positioned when pointer 58 indicates 0° on the scale (FIG. 10).

As shown best in FIG. 10, flexible golf ball tee 26 is connected to the outer free end of lower support arm 34 of golf ball tee assembly 20. In this regard, the outer end of the lower support arm has a horizontal bore 60 constructed to receive a sliding shaft 62. The sliding shaft has a vertical bore 64 at the free end thereof designed to receive a vertical tee holder 66. A set screw 68 on the sliding shaft secures the vertical tee holder at the desired elevation. The sliding shaft has a key 70 that cooperates with a keyway 72 in horizontal bore 60 to prevent relative rotation between the sliding shaft and lower support arm 34. A set screw 74 is provided to releasably lock the sliding shaft to the lower support arm. With this arrangement, golf ball tee 26 is shiftable in a horizontal direction toward and away from the lower support arm of golf ball tee assembly 20 whereby tee 26 and golf ball 28 are easily positioned in swing path 16 of club and shaft assembly 14.

Club and shaft assembly 14 includes an upper housing 80 fixedly connected to motivator assembly 30, as explained more fully below. Upper housing 80 includes a collar 82 which receives and supports the main components of the club and shaft assembly. Basically, this assembly has a club shaft 84 the upper end of which is fitted within collar 82. A club head 86 is connected to the lower end of club shaft 84. Club head 86 is secured to the club shaft by a mounting bracket 88 having opposed side arms 90 with the club head adjustably secured to the outer ends of the side arms. Club head 86 has opposed pivots 92 that fit within complementary boss members 94 on the side arms of mounting bracket 88. Loft angle locking screws 96 extend through the boss members into threaded engagement with the opposed pivots on club head 86 to securely fix the club head to the mounting bracket. This mechanism allows the loft angle of the club head to be adjusted by simply loosening loft angle locking screws 96 and rotating club head 86 about pivots 92 to the desired loft angle. Locking screws 96 are then tightened to secure the club head at the selected loft angle. Mounting bracket 88 is secured to the lower end of club shaft 84 by fasteners 98.

Alternatively, the club and shaft assembly may include a plurality of heads with fixed lofts. A head with the desired loft may then be selected and releasably attached by a suitable mechanism to the lower end of the golf ball shaft. Another head with a different loft may then be substituted whenever desired by simply removing the head on the device and attaching the next selection.

Club shaft 84 has a longitudinal axis 110 about which the club shaft may rotate for shifting the face of the club head to the right or left to thereby produce a hook or slice upon impact with golf ball 28. The club shaft has an upper end 112 fitted within collar 82 of upper housing 80 for relative rotary movement. The upper end of the club shaft has an internally threaded central bore 114 which matingly receives a hook/slice adjustment locking bolt 116. A lead counterweight 118 is fitted over collar 82 of upper housing 80 and the locking bolt extends through this counterweight into engagement with the internally threaded central bore at the upper end of the club shaft. Loosening of bolt 116 enables the club shaft to rotate about its longitudinal axis 110 relative to collar 82.

Figures 5, 6:
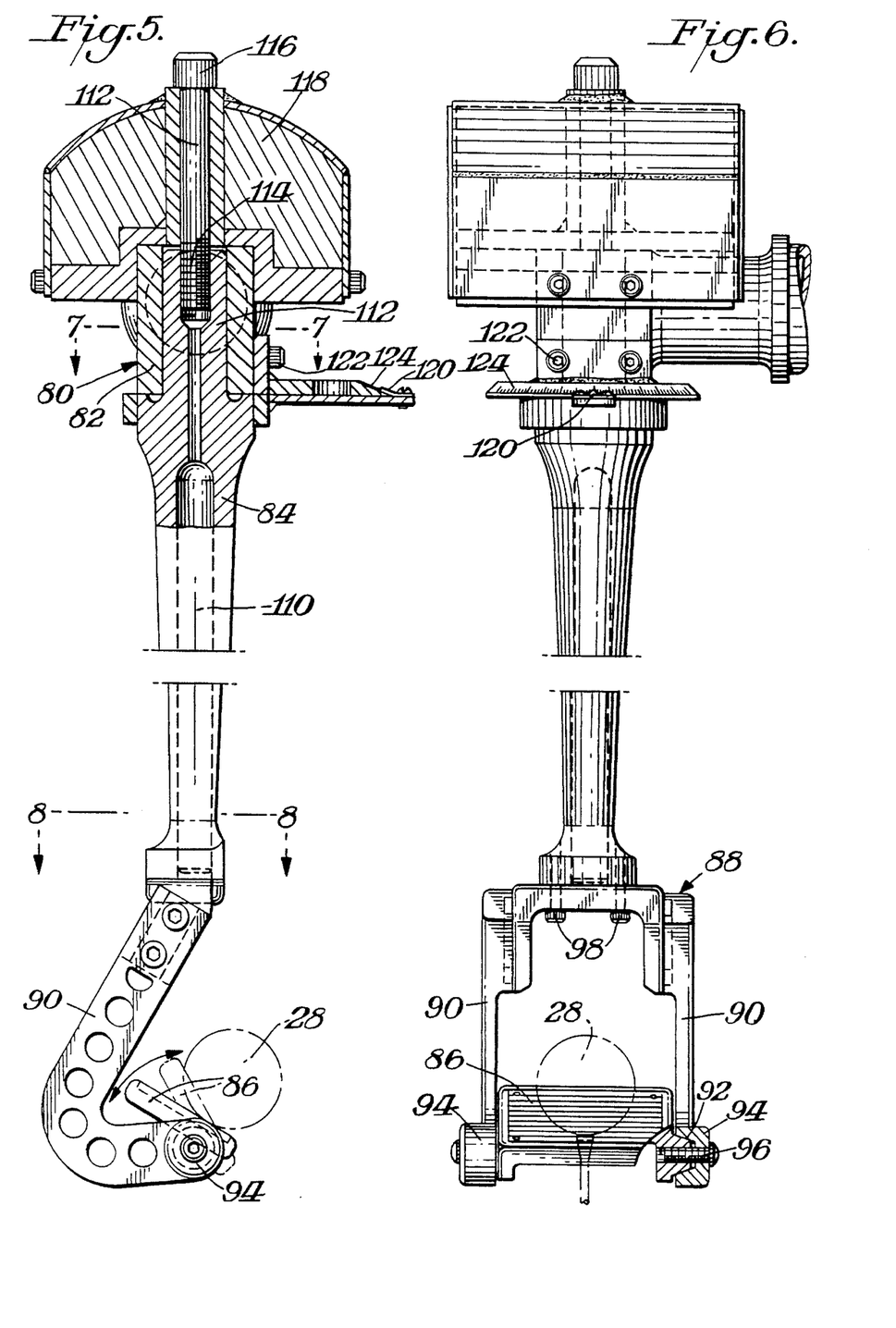
FIG. 5 is a front elevational view partially broken away illustrating details of the club and shaft assembly of the golf ball striking device.
FIG. 6 is a right side elevational view of the club and shaft assembly shown in FIG. 5.

As shown best in FIGS. 5–7, collar 82 has a hook/slice scale 120 secured thereto by fasteners 122. A pointer 124 secured to club shaft 84 cooperates with the hook/slice scale 120. In operation, with this particular arrangement pointer 124 indicates the angle adjustment of club head 86 when club shaft 84 is rotated about its longitudinal axis 110.

Framework 12 of golf ball striking device 10 primarily includes a fixed lower base frame assembly 130 and an upper frame 132. A rotatable connection 134 is provided at the interface between the upper and lower frames. This connection allows rotation of the upper frame which carries the club and shaft assembly and the golf ball tee assembly. Fundamentally, this arrangement enables adjustment of the trajectory angle of swing path 16 of club and shaft assembly 14. It enables the path of flight of the golf ball to be adjusted to the right or left of its straight forward flight path.

The feature of allowing rotation of the upper frame is particularly useful when club shaft 84 is rotated to shift the face of the club head to the right or left to produce a hook or slice. For example, if the club head is rotated 15° to the right to open the face and thereby produce a slice, upper frame 132 is rotated 15° in the opposite direction and locked in place. Then when the head strikes the ball the initial path of flight of the ball is straight forward before slicing to the right. Without this adjustment the initial path of flight of the ball would be to the right and then further right as the slice developed.

Rotatable connection 134 includes a top plate 136 secured to lower base frame assembly 130 by bolts 138. The outer circumference of the top plate includes an undercut 140 constructed and arranged to receive a locking ring 142 secured to upper frame 132 by bolts 144. In operation, when the bolts 144 are loosened upper frame 132 may then be rotated about a vertical central pivot pin 146 to the right or left relative to the fixed lower base frame assembly. Anti-friction material 148 secured to the lower base frame assembly by fasteners 150 and positioned at the interface between the lower base frame assembly and the upper frame assist in this angle adjustment. Once the desired position is achieved, bolts 144 are tightened which draws locking ring 142 against undercut 140 to thereby positively secure the upper and lower frames together.

Upper frame 132 carries a pointer 152 and the fixed lower base frame assembly has a scale 154 for indicating the trajectory angle of the swing path of the club and shaft assembly.

Motivator assembly 30 primarily includes a servo motor 160 directly connected to a gear box 162. The upper frame has structure 164 for supporting the servo motor and gear box in a generally horizontal orientation. The motivator assembly further includes a shaft assembly 166 horizontally extending from gear box 162. A flexible coupler 168 is interconnected to the shaft assembly.

As shown best in FIG. 10, the forward end of the shaft assembly 166 includes a main shaft 170 supported by a shaft housing 172 which forms part of the upper frame of framework 12. Main shaft 170 is journaled to the shaft housing by a pair of spaced apart bearings 174 each comprising an inner ring 176 and an outer ring 178 separated by a plurality of ball bearings 180. The inner ring of each of bearings 174 is keyed to main shaft 170 by keys 182. In operation, when the servo motor is energized power is transmitted through the gear box and flexible coupler to rotate main shaft 170. Rotation of the man shaft produces rotation of the club and shaft assembly. As explained above, the forward end of the main shaft carries housing 80 and its collar 82 connected to the upper end of club shaft 84.

FIG. 10 also illustrates details of the upper end of the golf ball tee assembly and particularly bearing 22 which is fitted to the outside of shaft housing 172 of framework 12. Bearing 22 is simply positioned between a pair of spaced apart collars 190, 192 with anti-friction material 194 located at the interface between the inside of the bearing and the outside of the main shaft housing. Forward collar 192 carries one or more set screws 196 for securing the collar to the main shaft housing. This connection of the golf ball tee assembly enables that assembly to freely rotate about the shaft housing when the assembly is moved from one position to another to vary the position of the golf ball along swing path 16 of club and shaft assembly 14.

Servo motor 160 operates to withdrawn the club and shaft assembly until it reaches a predetermined position in the back swing of that assembly. Once such predetermined position is reached the servo motor then functions to drive the club and shaft assembly in the opposite position for impacting golf ball 28 with club head 86. These movements are controlled by an appropriate program and also by a home sensor 200 secured to shaft housing 172 of framework 12. A home arm unit 202 is positioned directly adjacent home sensor 200, and the home arm unit is physically connected to rotate with main shaft 170. The home sensor emits a beam of light. Appropriate cutouts in the home arm unit are directly related to the position in the back swing of the club and shaft assembly when the rotation of that assembly is reversed for driving the club head forward for impacting golf ball 28 on tee 26.

Figure 11:
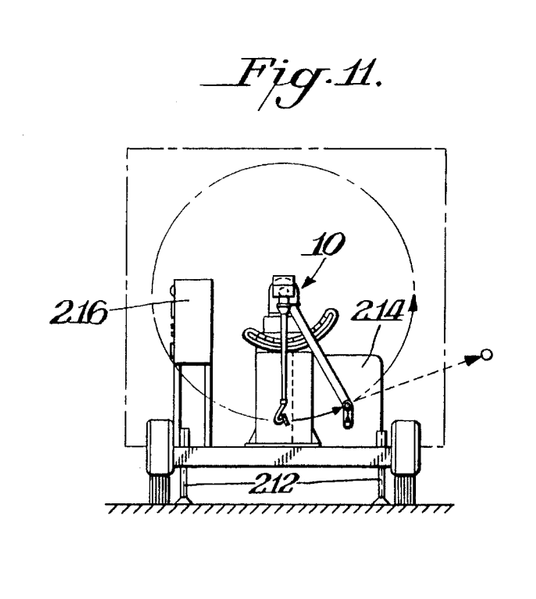
FIG. 11 is a front elevation view of the golf ball striking device mounted on and supported by a trailer assembly for transport and set-up.
Figure 12:
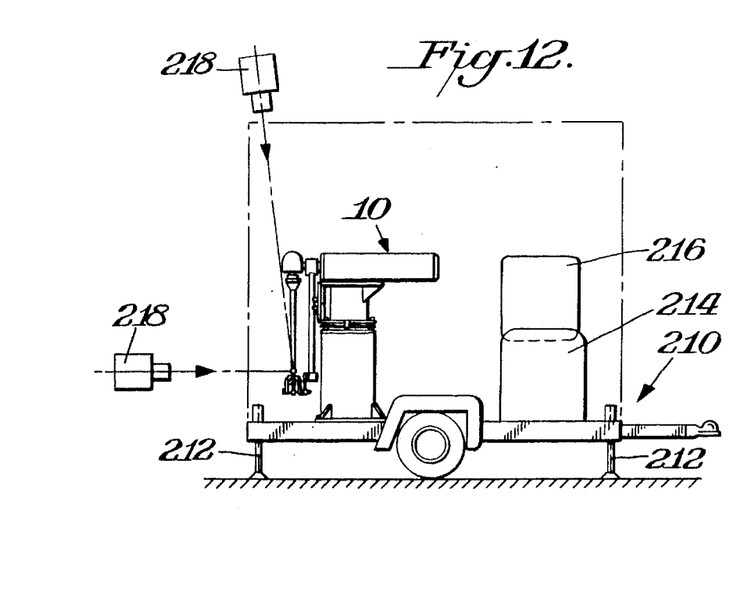
FIG. 12 is a right side elevational view of the golf ball striking device and trailer assembly shown in FIG. 11.
Figure 13:
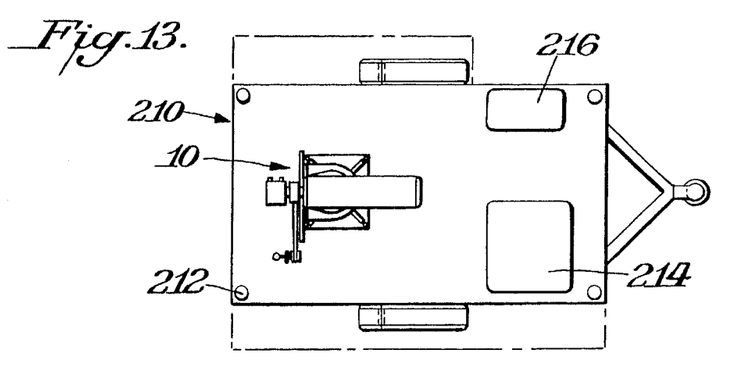
FIG. 13 is a top plan view of the golf ball striking device and trailer assembly shown in FIGS. 11 and 12.

FIGS. 11–13 illustrate golf ball striking device 10 mounted on and supported by a trailer assembly 210. This trailer assembly includes the standard components together with leveling jacks 212 at the four corners of the trailer. Additionally, a generator 214 and a control panel 16 may be provided. TV and/or strobe cameras 218 as well as cameras of other types may be used in the comparative testing and analytical procedures.

Figure 14:
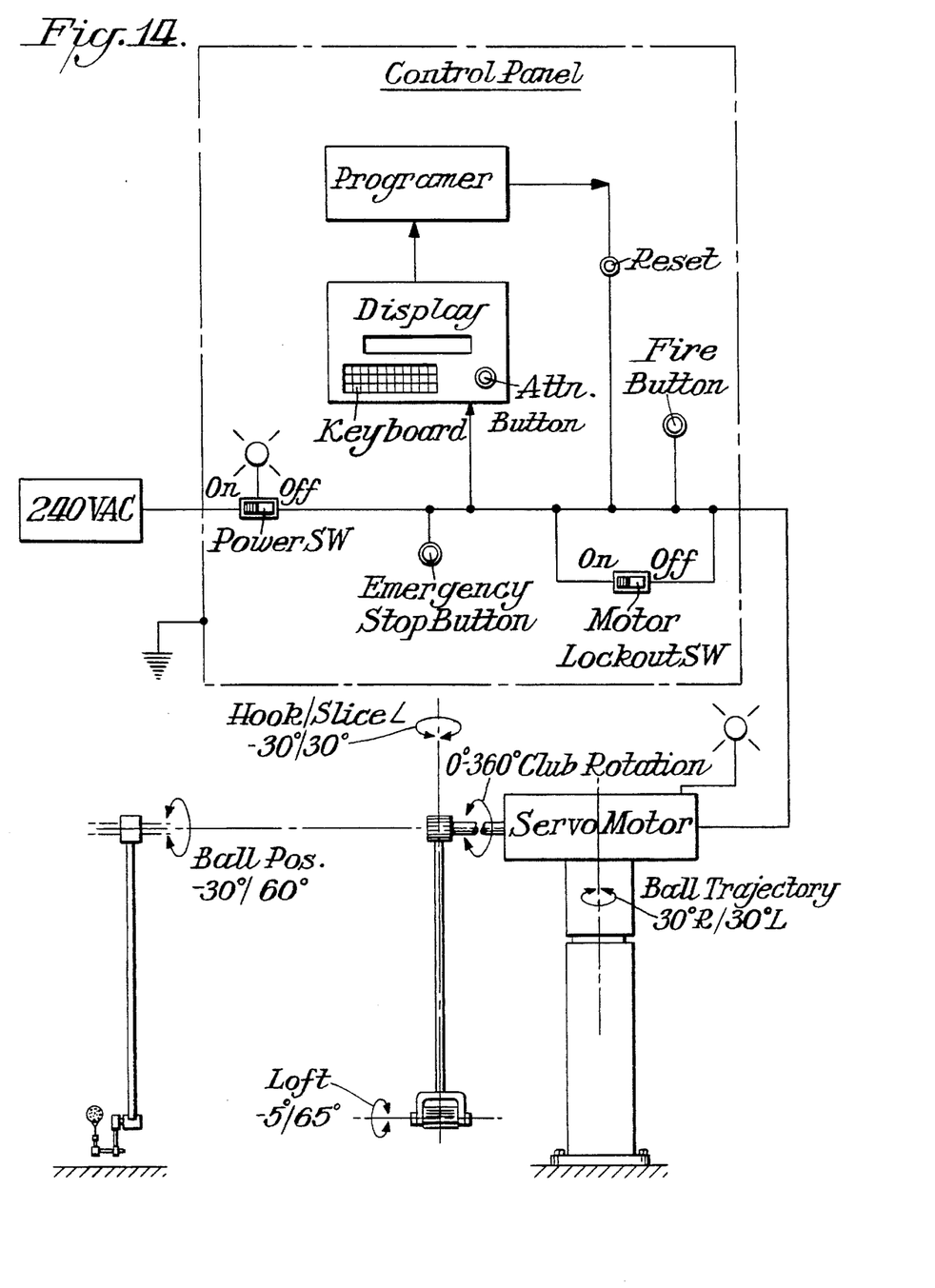
FIG. 14 is a schematic view of the control panel for programming the golf ball striking device according to the present invention.

FIG. 14 illustrates a representative arrangement for control panel 216 as well as the individual adjustable variables of golf ball striking device 10. The ball striking device is designed to rotate machined club head 86 at accurate and repeatable programmed speeds.

The operator is asked; desired speed, ball location offset and acceleration. Once entered, the program calculates the back up distance necessary to accelerate the club to this speed. The operator then commands the machine to back up this distance which causes the machine to just reach constant velocity when the ball is hit. After the hit, positioning is automatic.

Procedure

1. Turn on Power Switch red light on motor is "on"

switch light is "on"

Servo Motor is energized

2. Display Reads;

"Push Attn. button to change parameters"

3. Push Attn Button

Display Reads;

"Starting point in Degree=XX"

"New Starting Point in degree"

4. Key in this value:

Range is −30° to 60°

If this value is on the negative side, the − sign must proceed the value. No sign is necessary on the plus side. Enter this value.

5. Display reads:

"Club Speed—XXX"

"Enter maximum club speed Feet/Sec.

6. Key in this value; range is 0 to 180 Feet/Sec.

Enter

7. Display Reads

"Acceleration=XXXXX"

"Enter Accel Rate in RPM/sec.

8. Key in this value

Enter

Range is 0 to 25,000 RPM/sec

For speeds up to 170 ft/sec 20,000 RPM/sec is sufficient to make the swing in less than 1 revolution for speeds greater than 170 ft/sec higher values will have to be entered.

9. Display Reads;

"Push Reset Button to Position Club"

10. Push "Reset" Button. Club will rotate to starting position.

11. Display Reads; Press Fire Button to actuate club.

12. TURN OFF POWER AND PLACE BALL ON TEE

13. Turn on power

14. Push "Fire" to hit ball

15. Display Reads;

"To hit ball again press fire button"

16. At any time the parameters may be changed by pushing "Attn" and following the sequence.

If at any time an error message appears on the display because an out of bounds value was entered, turn power off and re-apply after 2 seconds and start over.

Certain ancillary hardware and software are utilized in support of this machine. Such equipment will accurately reflect the following:

1. Velocity of head at impact.
2. Initial velocity of ball.
3. Launch angle of ball.
4. Spin Rate of ball.
5. Spin axis of ball.

What we claim is:

1. A golf ball striking device comprising a framework, a club and shaft assembly rotatably mounted to the framework for movement along a swing path in a first vertical plane, and a golf ball tee assembly having upper and lower ends with the upper end rotatably mounted to the framework for free movement of the golf ball tee assembly in a second vertical plane into any one of a plurality of positions, means for releasably locking the golf ball tee assembly in place at any one of the plurality of positions, a golf ball tee at the lower end of the golf ball tee assembly for supporting a golf ball in the first vertical plane in the swing path of the club and shaft assembly, means on the golf ball tee assembly for maintaining the tee vertical at any of the plurality of positions of the golf ball tee assembly, and motivator means connected to drive the club and shaft assembly along its swing path for impacting a golf ball on the tee.

2. A golf ball striking device as in claim 1 wherein the club and shaft assembly has a horizontal axis of rotation and the golf ball tee assembly has the same axis of rotation.

3. A golf ball striking device as in claim 1 including position adjusting means for the golf ball tee of the golf ball tee assembly constructed and arranged to shift the golf ball tee in a horizontal direction toward and away from the golf ball tee assembly.

4. A golf ball striking device as in claim 1 wherein the first and second vertical planes are parallel to one another.

5. A golf ball striking device as in claim 1 wherein the club and shaft assembly includes a club head constructed and arranged to impact upon a golf ball on the golf ball tee of the golf ball tee assembly, the club head having an adjustable loft, and means for releasably locking the club head in place at any one of a plurality of selected club head lofts.

6. A golf ball striking device as in claim 1 wherein the club and shaft assembly includes an upper housing connected to the motivator means whereby the club and shaft assembly rotates along the swing bath in the first vertical plane, and a club shaft adjustably connected to the upper housing having a longitudinal axis about which the club shaft rotates relative to the upper housing.

7. A golf ball striking device as in claim 6 wherein the club and shaft assembly includes a club head fixedly connected to the club shaft constructed and arranged to impact upon a golf ball on the golf ball tee assembly.

8. A golf ball striking device as in claim 6 wherein the club and shaft assembly includes an angular scale fixed to the upper housing and a cooperating pointer on the club shaft for indicating the rotary position of the club shaft about its longitudinal axis relative to the upper housing.

9. A golf ball striking device as in claim 6 wherein the upper housing includes a counterweight.

10. A golf ball striking device as in claim 1 including a tee angle position scale fixedly secured to the framework having an arcuate slot therein, tee guide retainers on the golf ball tee assembly extending into the arcuate slot for movement along the slot as the golf ball tee assembly is rotated to any one of its plurality of positions, means on the tee guide retainers for releasably locking the golf ball tee assembly to the tee angle position scale, and a pointer on the golf ball tee assembly cooperating with the tee angle position scale for indicating the angular position of the golf ball tee assembly.

11. A golf ball striking device as in claim 10 wherein the tee angle position scale has indicia ranging from −30° to 60° and wherein the golf ball tee assembly is vertically positioned when the pointer indicates 0° on the scale.

12. A golf ball striking device as in claim 10 wherein the tee angle position scale is positioned in a third vertical plane parallel to the first and second planes.

13. A golf ball striking device as in claim 1 wherein the framework includes a fixed lower base frame assembly and an upper frame, a vertical pivot pin interconnecting the upper frame with the fixed lower base frame assembly whereby the upper frame is rotatable about the vertical pivot pin, and wherein the club and shaft assembly and golf ball tee assembly are mounted to the upper frame of the framework.

14. A golf ball striking device as in claim 13 wherein the upper frame has a pointer and the fixed lower base frame assembly has a scale for indicating a trajectory angle of the swing path of the club and shaft assembly.

15. A golf ball striking device as in claim 14 including means on the framework for releasably locking the upper frame to the fixed lower base frame assembly.

16. A golf ball striking device as in claim 1 wherein the motivator means includes a servo motor and gear box, shaft means connecting the servo motor and gear box to the club and shaft assembly, and a flexible coupler interconnecting the shaft means.

17. A golf ball striking device as in claim 16 wherein the framework includes a shaft housing for supporting the shaft means and wherein the upper end of the golf ball tee assembly comprises a bearing member surrounding the shaft housing for free rotatable movement.

* * * * *